United States Patent
Muller et al.

(10) Patent No.: US 12,082,829 B2
(45) Date of Patent: Sep. 10, 2024

(54) GEARED INSTRUMENT FOR MINIMALLY INVASIVE SURGERY

(71) Applicant: WRIGHT MEDICAL TECHNOLOGY, INC., Memphis, TN (US)

(72) Inventors: Erin Muller, Fort Wayne, IN (US); Joseph Ryan Woodard, Memphis, TN (US); Terrance W. Strohkirch, Memphis, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 373 days.

(21) Appl. No.: 17/603,527

(22) PCT Filed: Mar. 20, 2020

(86) PCT No.: PCT/US2020/023775
§ 371 (c)(1),
(2) Date: Oct. 13, 2021

(87) PCT Pub. No.: WO2020/242561
PCT Pub. Date: Dec. 3, 2020

(65) Prior Publication Data
US 2022/0211396 A1 Jul. 7, 2022

Related U.S. Application Data

(60) Provisional application No. 62/854,073, filed on May 29, 2019.

(51) Int. Cl.
*A61B 17/17* (2006.01)
*A61B 17/02* (2006.01)
*A61B 17/16* (2006.01)

(52) U.S. Cl.
CPC ........ *A61B 17/1775* (2016.11); *A61B 17/025* (2013.01); *A61B 17/1642* (2013.01); *A61B 17/1682* (2013.01)

(58) Field of Classification Search
CPC .............. A61B 17/1775; A61B 17/025; A61B 17/1642; A61B 17/1682
See application file for complete search history.

(56) References Cited

U.S. PATENT DOCUMENTS

| | | | | |
|---|---|---|---|---|
| 4,808,185 | A * | 2/1989 | Penenberg | A61B 17/1624 623/20.29 |
| 6,740,087 | B2 * | 5/2004 | Knox | A61B 17/686 606/279 |

(Continued)

OTHER PUBLICATIONS

First Examination Report issued in connection with corresponding Australian Patent Application No. 2020285308, May 24, 2022, 3 pages.

(Continued)

*Primary Examiner* — Kevin T Truong
*Assistant Examiner* — Diana Jones
(74) *Attorney, Agent, or Firm* — DUANE MORRIS LLP

(57) ABSTRACT

A system includes an instrument and a distractor. The instrument includes a shaft extending from a first end to a second end and defining a first axis between the first end and the second end. The instrument further includes a first gear coupled to the first end of the shaft. The instrument further includes a second gear enmeshed with the first gear. The instrument further includes a reamer coupled to the second gear. Rotation of the shaft about the first axis causes rotation of the reamer about a second axis that is non-parallel with the first axis. The distractor includes a first arm defining a first passage and a second arm defining a second passage, each configured to receive a pin. The distractor further includes a retainer configured to engage the instrument to (Continued)

retain the instrument in position. The distance between the first passage and the second passage is adjustable.

20 Claims, 9 Drawing Sheets

(56) References Cited

U.S. PATENT DOCUMENTS

| | | | |
|---|---|---|---|
| 7,572,260 B1 | 8/2009 | Nelson | |
| 2002/0193797 A1* | 12/2002 | Johnson | A61F 2/4609 606/79 |
| 2003/0130662 A1 | 7/2003 | Michelson | |
| 2005/0203533 A1* | 9/2005 | Ferguson | A61B 17/1757 606/90 |
| 2010/0087830 A1* | 4/2010 | Dace | A61B 17/1671 606/99 |
| 2013/0184818 A1* | 7/2013 | Coughlin | A61B 17/0206 623/13.14 |
| 2014/0257509 A1 | 9/2014 | Dacosta et al. | |
| 2015/0134071 A1 | 5/2015 | Luna et al. | |
| 2015/0282818 A1* | 10/2015 | Weinstein | A61B 17/1686 606/328 |
| 2016/0051267 A1 | 2/2016 | Sander | |

OTHER PUBLICATIONS

International Search Report and Written Opinion for PCT International Application No. PCT/US2020/023775 dated Jun. 15, 2020.
Extended European Search Report issued in connection with European Patent Application No. 20814713.2, May 4, 2023, 9 pages.

* cited by examiner

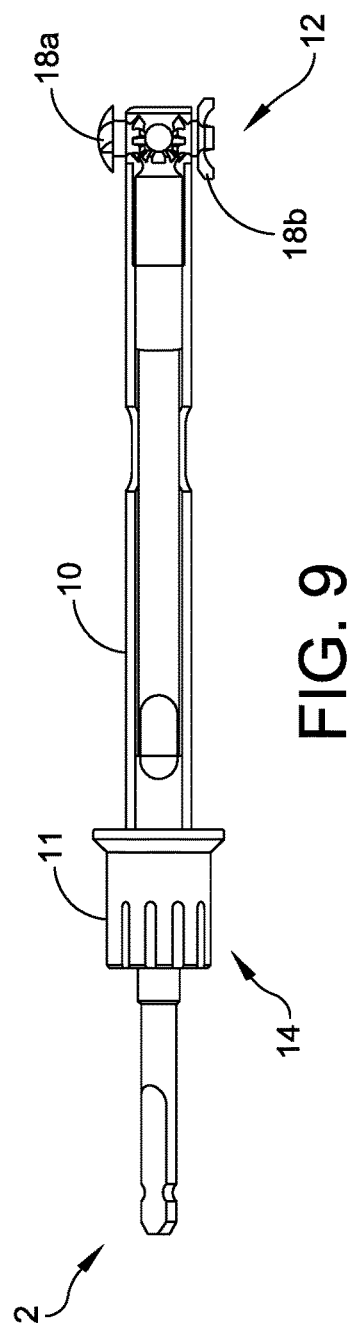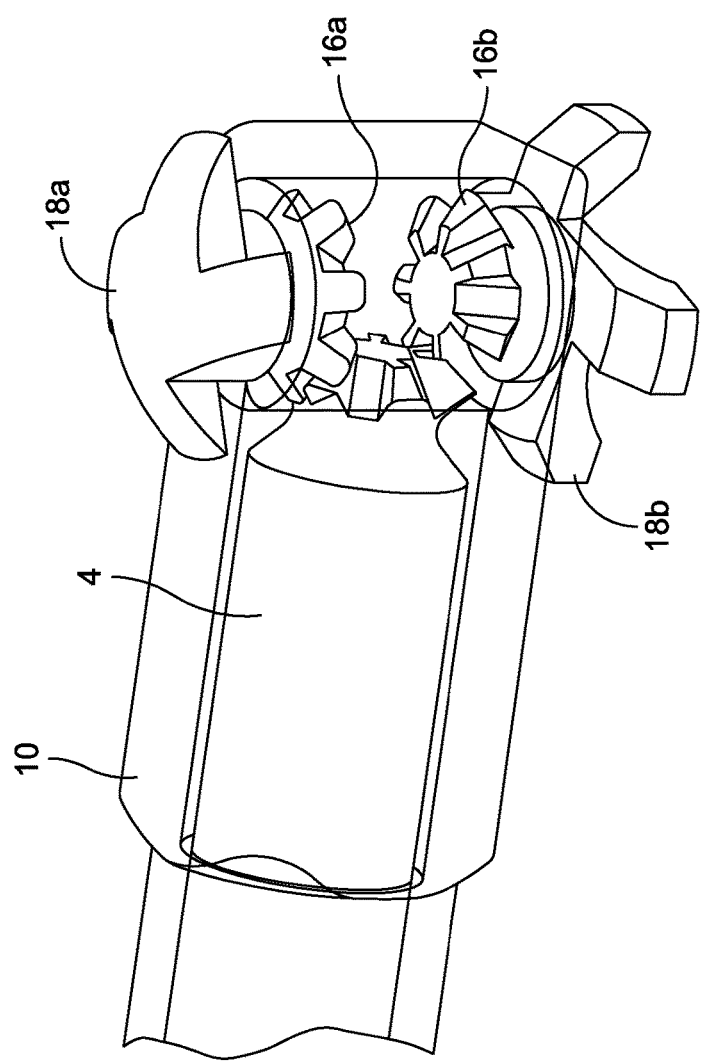

GEARED INSTRUMENT FOR MINIMALLY INVASIVE SURGERY

CROSS-REFERENCE TO RELATED APPLICATION

This application is a National Stage Application, filed under 35 U.S.C. 371, of International Patent Application No. PCT/US2020/023775, filed on Mar. 20, 2020, which claims the benefit of U.S. Patent Application Ser. No. 62/854,073, filed May 29, 2019, the entireties of which are incorporated herein by reference.

FIELD OF THE INVENTION

This disclosure generally relates to systems and methods for orthopedic surgery. More particularly, this disclosure relates to systems and methods for performing minimally invasive repair of the foot.

BACKGROUND

Fusion of the metatarsal-phalangeal (MTP) joint can be used to relieve pain in the forefoot. This procedure can also be used to correct deformities in the foot. The deformities can be caused by injury, arthritis, or genetic defects.

In some procedures, prior to fusing, the cartilage within the joint must be removed. This may be done using cup- or cone-shaped reamers. This typically requires the use of an "open" procedure involving fully dislocating the joint in order to approach each side of the joint. These procedures also typically require the use of multiple reamers and several steps to complete the process. Minimally invasive processes have been developed, but typically require the use of burrs. Such burrs remove bone in addition to the cartilage, thereby shortening the bone. This can lead to additional complications. Moreover, use of burrs commonly necessitates a freehand technique in which the surgeon must remove the cartilage with little to no guidance. As such, there is a risk of incomplete joint debridement or the creation of irregular surfaces at each end of the bones to be fused, which could make fusion more difficult.

SUMMARY

In one aspect, a system is disclosed that includes an instrument and a distractor. The instrument includes a shaft extending from a first end to a second end and defining a first axis between the first end and the second end. The instrument further includes a first gear coupled to the first end of the shaft such that rotation of the shaft about the first axis causes rotation of the first gear about the first axis. The instrument further includes a second gear enmeshed with the first gear. The instrument further includes a reamer coupled to the second gear. Rotation of the shaft about the first axis causes rotation of the reamer about a second axis that is non-parallel with the first axis such that, with the instrument at least partially disposed in a joint space between a first bone and a second bone, rotation of the reamer removes material from the joint space. The distractor includes a first arm defining a first passage configured to receive a first pin inserted in the first bone and a second arm defining a second passage configured to receive a second pin inserted in the second bone. The distractor further includes a retainer extending from the first arm, wherein the retainer is configured to engage the instrument to retain the instrument in position. The distance between the first passage and the second passage is adjustable.

In another aspect, a method includes forming an incision to access a metatarsophalangeal joint. The method further includes locating an instrument partially within the metatarsophalangeal joint. The instrument includes a shaft extending from a first end to a second end and defining a first axis between the first end and the second end. The instrument further includes a first gear coupled to the first end of the shaft such that rotation of the shaft about the first axis causes rotation of the first gear about the first axis. The instrument further includes a second gear enmeshed with the first gear. The instrument further includes a reamer coupled to the second gear. Rotation of the shaft about the first axis causes rotation of the reamer about a second axis that is non-parallel with the first axis. The method further includes rotating the shaft about the first axis to rotate the reamer about the second axis to remove material from the metatarsophalangeal joint.

In another aspect, an instrument includes a shaft, a first gear, a second gear, and a reamer. The shaft extends from a first end to a second end and defines a first axis between the first end and the second end. The first gear is coupled to the first end of the shaft such that rotation of the shaft about the first axis causes rotation of the first gear about the first axis. The second gear is enmeshed with the first gear. The reamer is coupled to the second gear. Rotation of the shaft about the first axis causes rotation of the reamer about a second axis that is non-parallel with the first axis such that, with the instrument at least partially disposed in a joint space between a first bone and a second bone, rotation of the reamer removes material from the joint space. The reamer is one of a cup reamer and a cone reamer.

BRIEF DESCRIPTION OF THE FIGURES

The features and advantages of the present invention will be more fully disclosed in, or rendered obvious by the following detailed description of the preferred embodiments, which are to be considered together with the accompanying drawings wherein like numbers refer to like parts.

FIG. 9 is a side view of a geared instrument, according to another embodiment described herein, in which the housing is transparent to show the shaft disposed therein.

FIG. 10 is a detail perspective view of the geared instrument of FIG. 9.

DETAILED DESCRIPTION

Figure 1:
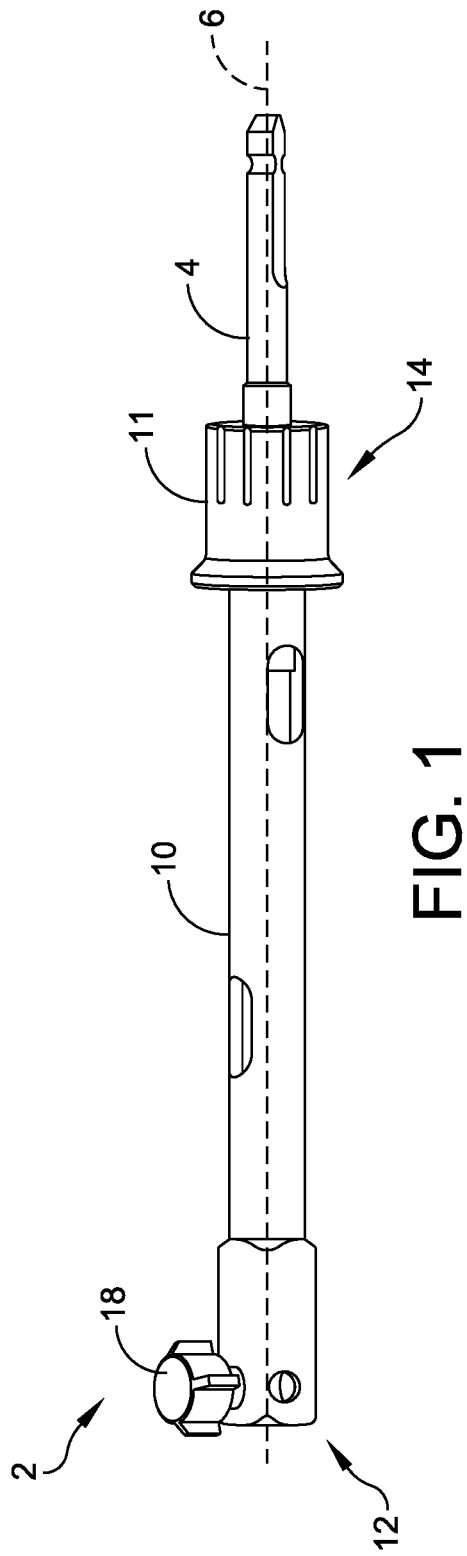
FIG. 1 shows a perspective view of a geared instrument, according to one embodiment described herein.

The description of the exemplary embodiments is intended to be read in connection with the accompanying drawings, which are to be considered part of the entire written description. In the description, relative terms such as "lower," "upper," "horizontal," "vertical," "proximal," "distal," "above," "below," "up," "down," "top" and "bottom," as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

The present disclosure describes a geared instrument for use in preparing a joint for fusion, distractors to be used in conjunction with such a geared instrument, and methods of using the same. The instruments and methods are particularly well-suited for preparation of the MTP joint, however, it should be understood that such instruments and methods can be used for preparing other joints for fusion. The geared instrument includes a shaft configured to rotate about a first axis and has a first gear at a first end of the shaft. The first gear is coupled to a second gear that rotates with a reamer configured to be used to prepare a metatarsal or proximal phalanx for a fusion procedure. The reamer rotates about a second axis that is non-parallel with the first axis.

Figure 2:
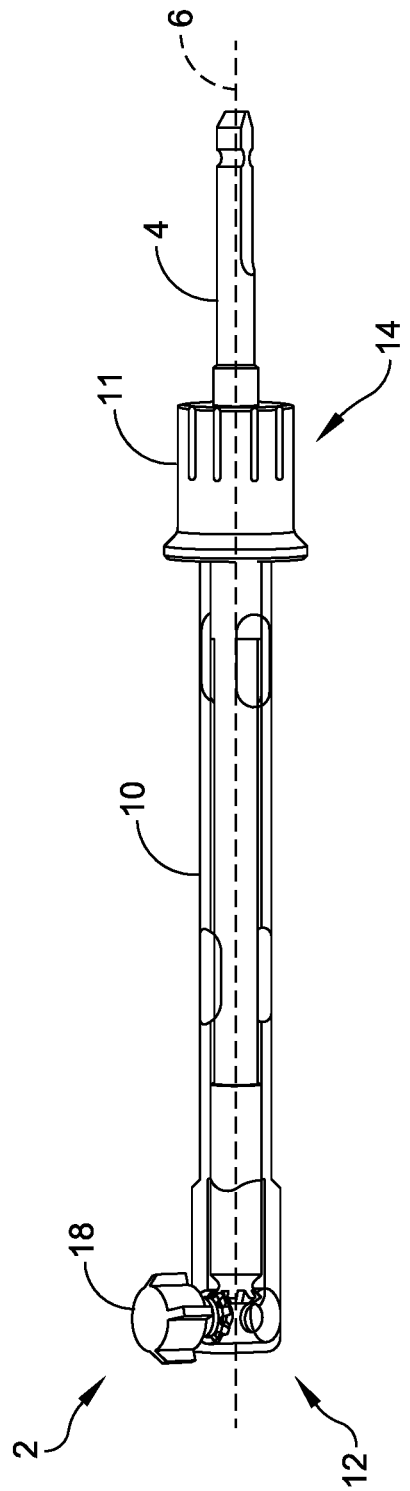
FIG. 2 shows a perspective view of the geared instrument of FIG. 1, in which the housing is transparent to show the shaft disposed therein.

FIGS. 1 and 2 illustrate one embodiment of a geared instrument 2 for use in performing a surgical procedure, for example, for preparing an MTP joint for fusion. The geared instrument 2 comprises a shaft 4. In some embodiments, one end of the shaft 4 may be configured for coupling to a mechanical drive. For example, the shaft 4 may be configured to couple to a mechanical drive via a threaded connection, a press-fit connection, and/or any other suitable connection. For example, in one embodiment, the shaft 4 may be configured to engage with a collet. The mechanical drive may be, for example, a surgical drill. In other embodiments, the shaft 4 may include a handle that allows the shaft to be rotated by hand. The shaft 4 is rotatable about the longitudinal axis 6 of the shaft 4.

Figure 3:
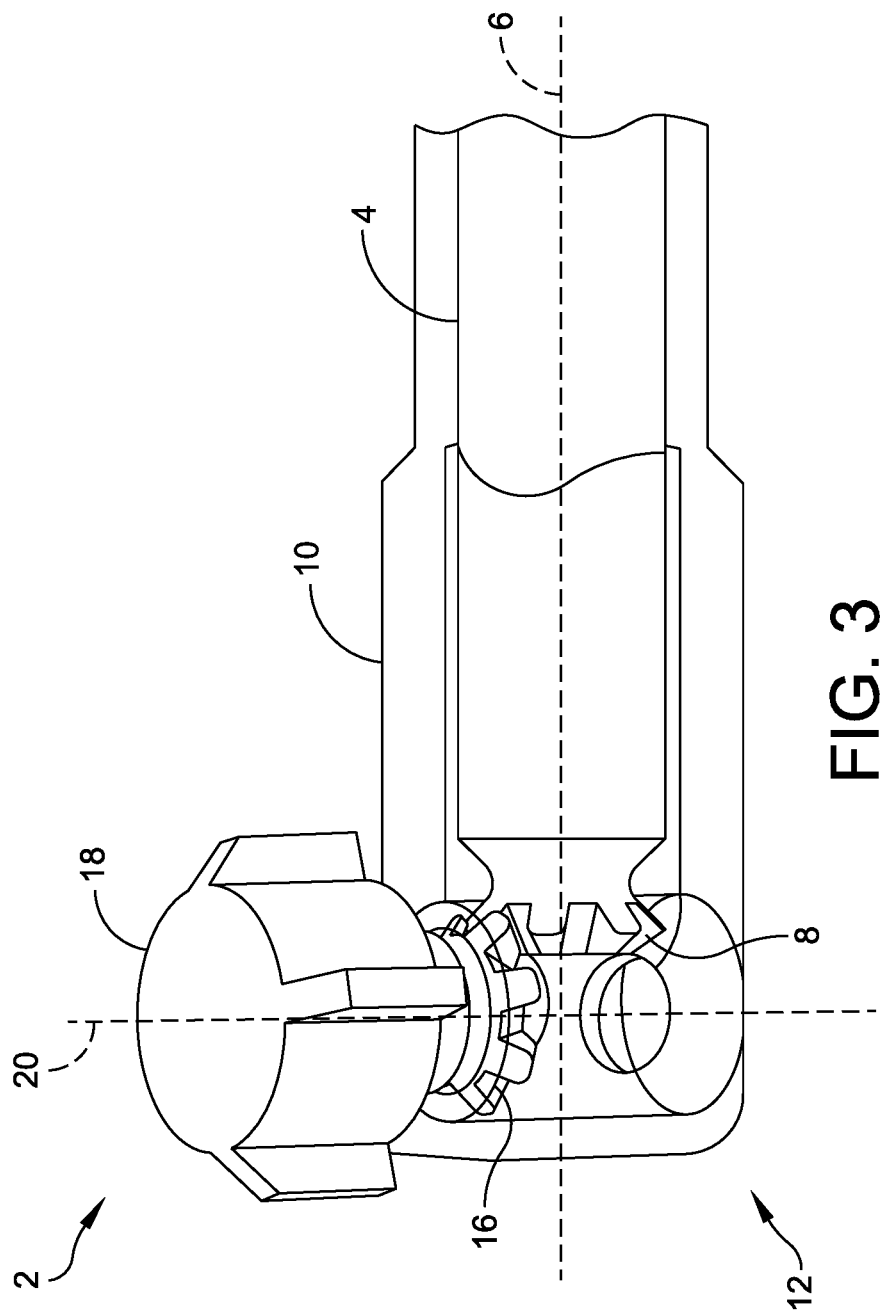
FIG. 3 shows a detail view of the first end of the geared instrument of FIG. 1.

As shown best in FIG. 3, a first gear 8 is located at, and coupled to, the distal end of the shaft 4. As will be described further herein, the first gear 8 may be, for example, a bevel gear, a worm gear, a spiral bevel gear, a hypoid gear, and/or a crown gear. The first gear 8 may be integrally formed with the shaft 4. For example, the shaft 4 and first gear 8 may be formed by injection molding, casting, be machined out of a single piece of material, or be formed by other processes. Alternatively, the first gear 8 may be a separate component that is joined to the shaft 4 by any appropriate method (e.g., welding, bonding, press-fit, fasteners, etc.).

Returning to FIGS. 1 and 2, the shaft 4 may be disposed within a housing 10. FIG. 2 shows the housing 10 in transparent form to allow the shaft 4 to be viewed inside the housing 10. In one embodiment, as shown, the housing 10 is a tubular housing extending from a first end 12 to a second end 14. An opening (not shown) at the second end 14 of the housing 10 allows for the passage of the shaft 4 through the opening and out of the housing 10 such that the end of the shaft 4 can be rotated by hand or via a mechanical drive, as described above. In some embodiments, a portion of the shaft 4 may be captured in the housing 10 to prevent the shaft 4 from being inadvertently removed from the housing 10. In other embodiments, the shaft 4 is removable from the housing 10. The geared instrument 2 may include a cap 11 coupled to the housing 10. During assembly of the geared instrument 2, the shaft 4 may be inserted into the housing 10. The cap 11 may then be coupled to the housing 10 to retain the shaft 4 in place. The shaft 4 may have a shoulder or flange that contacts the cap 11 to prevent removal of the shaft 4 from the housing 10.

As shown in FIG. 3, a second gear 16 is located within the housing 10 at the first end 12 of the housing 10. The second gear 16 is configured to mesh with the first gear 8 (i.e., the teeth of the gears 8, 16 mesh together to translate rotation of the first gear 8 to rotation of the second gear 16). The second gear 16 may comprise any suitable gear such as, for example, a bevel gear, a worm gear, a spiral bevel gear, a hypoid gear, and/or a crown gear. A reamer 18 is coupled to the second gear 16 such that the reamer 18 rotates with the second gear 16. In some embodiments, second gear 16 and reamer 18 are integrally formed. For example, second gear 16 and reamer 18 may be formed by injection molding, casting, be machined out of a single piece of material, or be formed by other processes. Alternatively, the second gear 16 may be a separate component that is joined to the reamer 18 by any appropriate method (e.g., welding, bonding, press-fit, fasteners, etc.). In some embodiments, a shaft may extend between the second gear 16 and the reamer 18 and extend through an aperture in the housing 10.

In some embodiments, the reamer 18 rotates at the same rotational speed as the second gear 16 (e.g., the first gear 8 and the second gear 16 may have a 1:1 gear ratio). In other embodiments, the reamer 18 rotates at a different rotational speed than the second gear 16. For example, additional gearing between the reamer 18 and the second gear 16 may provide for different rotational speeds. Alternatively, or additionally, the gear ratio of the first gear 8 and the second gear 16 may have a gear ratio other than 1:1. The second gear 16 and the reamer 18 are rotatable about a second axis 20. The second axis 20 is non-parallel with the first axis 6. For example, in some embodiments, the first axis 6 and the second axis 20 are orthogonal. In other embodiments, the first axis 6 and the second axis 20 are disposed at an oblique angle.

The reamer 18 can include any appropriate geometry. For example, the reamer 18 may be in the form of a cup or cone reamer and be used to prepare the metatarsal and/or proximal phalanx for MTP fusion, midfoot fusion, a Lapidus procedure, or any other desired procedure. For example, a cone reamer may be used to prepare the metatarsal and a cup reamer may be used to prepare the proximal phalanx. Such cup and cone reamers are described in, for example, U.S. Pat. No. 9,848,893, issued on Dec. 26, 2017, entitled BONE IMPLANTS AND CUTTING APPARATUSES AND METHODS, which is incorporated herein by reference in its entirety.

In other embodiments, the reamer 18 is shaped and configured to form a cavity in a bone (e.g., metatarsal or proximal phalanx) such that the cavity can receive an implant. For example, the reamer can be shaped to form a cavity to receive a cartilage-like polymer implant such as the CARTIVA synthetic cartilage implant sold by Wright Medical Group N.V.

Figure 11:
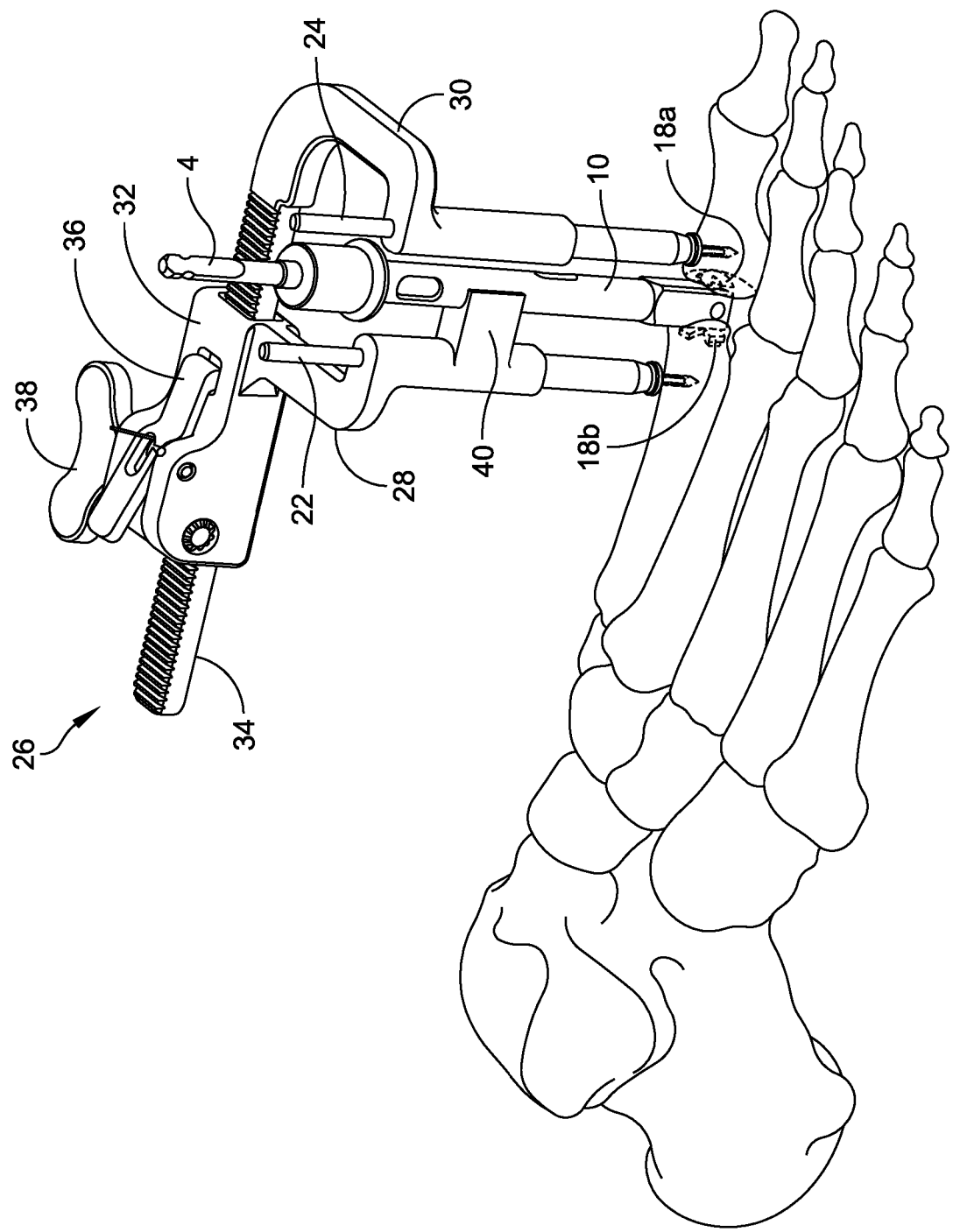
FIG. 11 is a perspective view of the geared instrument of FIG. 9 in use.

In some embodiments, shown in FIGS. 9-11, the geared instrument 2 includes two reamers 18a, 18b positioned on opposite sides of the shaft 4 and facing away from one another. For example, the first reamer 18a may be in the shape of a cup reamer and extend in a first direction (e.g., for preparing the end of a proximal phalanx). The second reamer 18b may be in the shape of a cone reamer and extend in a second direction (e.g., for preparing the end of a metatarsal). Each reamer 18a, 18b may be coupled to a gear 16a, 16b that meshes with first gear 8. In this way, the metatarsal and proximal phalanx may be prepared simultaneously, as illustrated in FIG. 11. The first 18a and second 18b reamers may, in some embodiments, rotate at the same rotational rate. In other embodiments, the first 18a and second 18b reamers rotate at different rotational rates. For example, the gear ratio of first gear 8 to gear 16a may be different than the gear ratio of the first gear 8 to the gear 16b. In some embodiments the gears 16a, 16b rotate in the same direction (e.g. clockwise); in other embodiments, the gears rotate in opposite directions (i.e. clockwise and counterclockwise).

In some embodiments, the housing 10 allows the reamer 18 and/or the second gear 16 to be removed from the housing 10. In other embodiments, the reamer 18 and/or the second gear 16 are not intended to be removed from the housing 10.

When the shaft 4 is in place in the housing 10, the first gear 8 meshes with the second gear 16. The coupling of the first gear 8 and the second gear 16 translates rotation of the shaft 4 about the first axis 6 to rotation of the reamer 18 about the second axis 20. In some embodiments, the shaft 4 and the reamer 18 rotate at the same rotational speed. In other embodiments, the shaft 4 and the reamer 18 rotate at different rotational speeds (e.g., first gear 8 and second gear 16 have a gear ratio other than one). The shaft 4 may be rotated about the first axis 6 by, for example, a clinician gripping the shaft 4 or using a mechanical drive. The shaft 4 may be rotatable in a first direction and/or a second direction (i.e., clockwise or counterclockwise). Rotation of the reamer 18 allows one or more surgical procedures to be performed without needing direct axial access to a bone. For example, the reamer 18 may be used to prepare an MTP joint for a fusion surgery. Additionally, or alternatively, reamer 18 may be used to form a cavity in a bone to receive an implant.

The geared instrument 2 is configured to facilitate one or more surgical procedures. For example, in some embodiments, the geared instrument 2 is sized and configured to facilitate a fusion of the MTP joint. The geared instrument 2, and specifically the housing 10, is configured to fit through an incision formed adjacent to the MTP joint. For example, as described further herein, the housing may be inserted through a superior incision formed above the MTP joint. The use of the geared instrument 2 may eliminate the need for complete dislocation of the joint. Instead, the housing 10 fits within the MTP joint through the incision and allows cartilage within the joint to be removed and otherwise assist with preparation of the joint for fusion.

Figure 7:
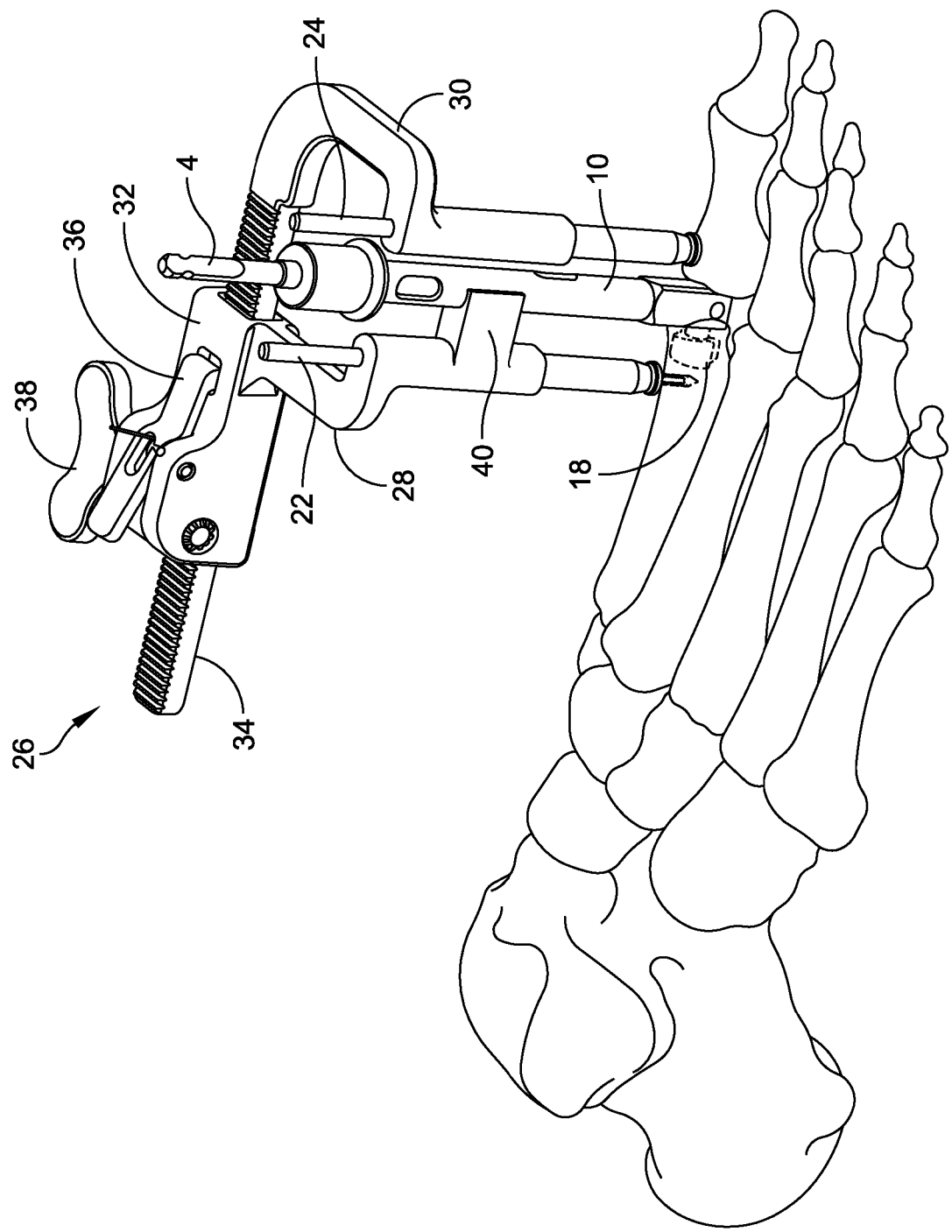
FIG. 7 shows a step of a method of performing a surgical procedure on an MTP joint in which the geared instrument is inserted in the MTP joint.

For example, in one embodiment, the geared instrument 2 is sized and configured for insertion of the housing 10 between the first metatarsal 200 and proximal phalanx 202 (as shown in FIG. 7). The shaft 4 is rotated about the first axis 6, rotating the reamer 18 about the second axis 20 to prepare the metatarsal 200 or proximal phalanx 202 for fusion (e.g., removing cartilage). Optionally, after preparing the metatarsal 200 or the proximal phalanx 202, the geared instrument 2 is removed from the joint, turned, and reinserted through the incision such that it can be used to prepare the other surface of the metatarsal-phalangeal joint (e.g., by removing cartilage). Once the geared instrument 2 is reinserted into the MTP joint, the shaft 4 is rotated to prepare the respective bone. In other embodiments, geared instrument 2 includes two reamers extending in opposite directions, each coupled to shaft 4 via first gear 8 such that both bones can be prepared simultaneously, as described above with reference to FIGS. 9-11.

Figure 4:
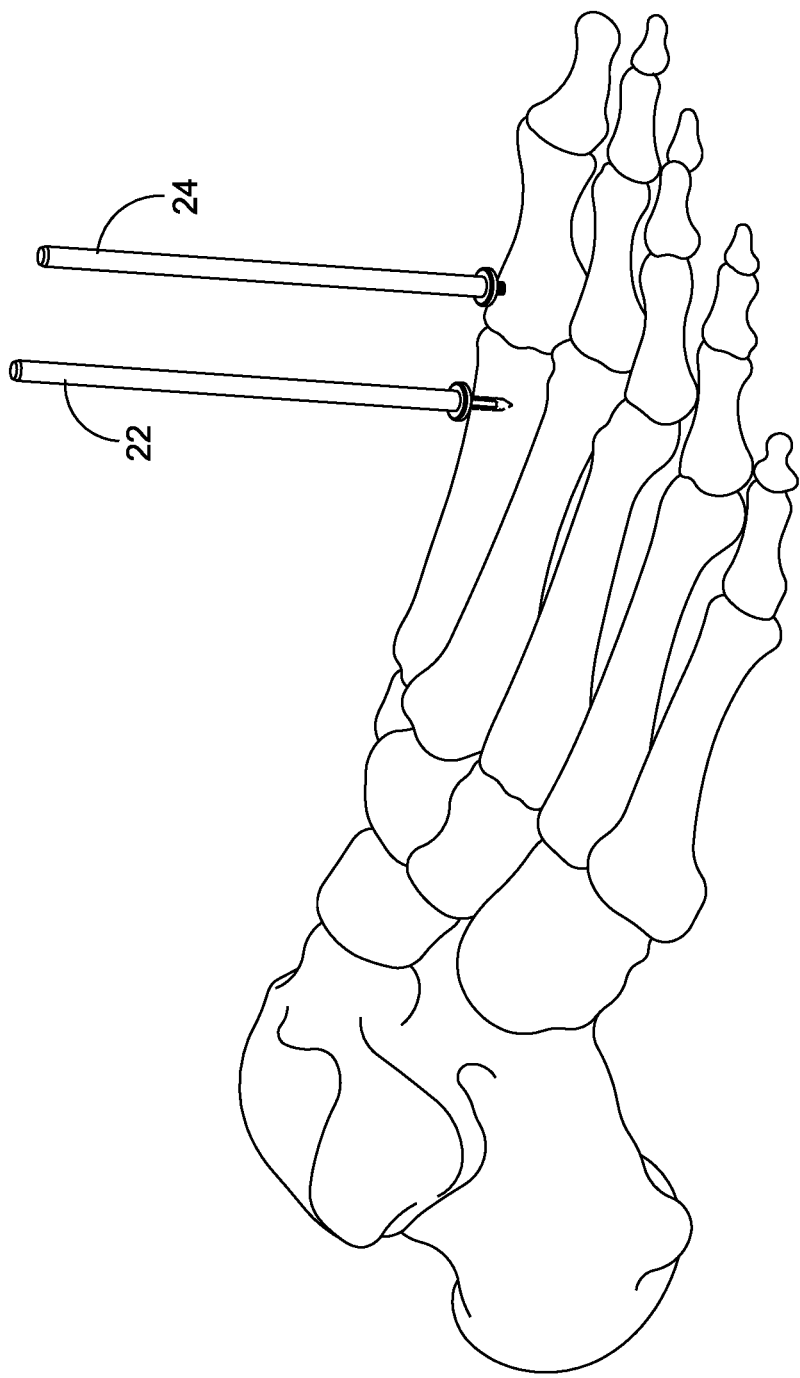
FIG. 4 shows a step of a method of performing a surgical procedure on an MTP joint in which a first pin is inserted in the metatarsal and a second pin is inserted in the proximal phalanx.

FIGS. 4-7 illustrate a method of performing a surgical procedure on an MTP joint. Although these figures illustrate a method of preparing the first MTP joint, the apparatuses and methods described herein may be used to prepare any MTP joint for fusion. In FIGS. 4-7, only the bony anatomy of the foot is shown for clarity. As shown in FIG. 4, a first pin 22 is inserted into the first metatarsal 200 and a second pin 24 is inserted into the proximal phalanx 202. In some embodiments, incisions are made in the skin prior to insertion of the pins 22, 24. The pins 22, 24 may be, for example, Steinmann pins, olive wires, K-wires (Kirschner wires), or any other pin or wire capable of being fixed in the metatarsal 200 or proximal phalanx 202.

Figure 5:
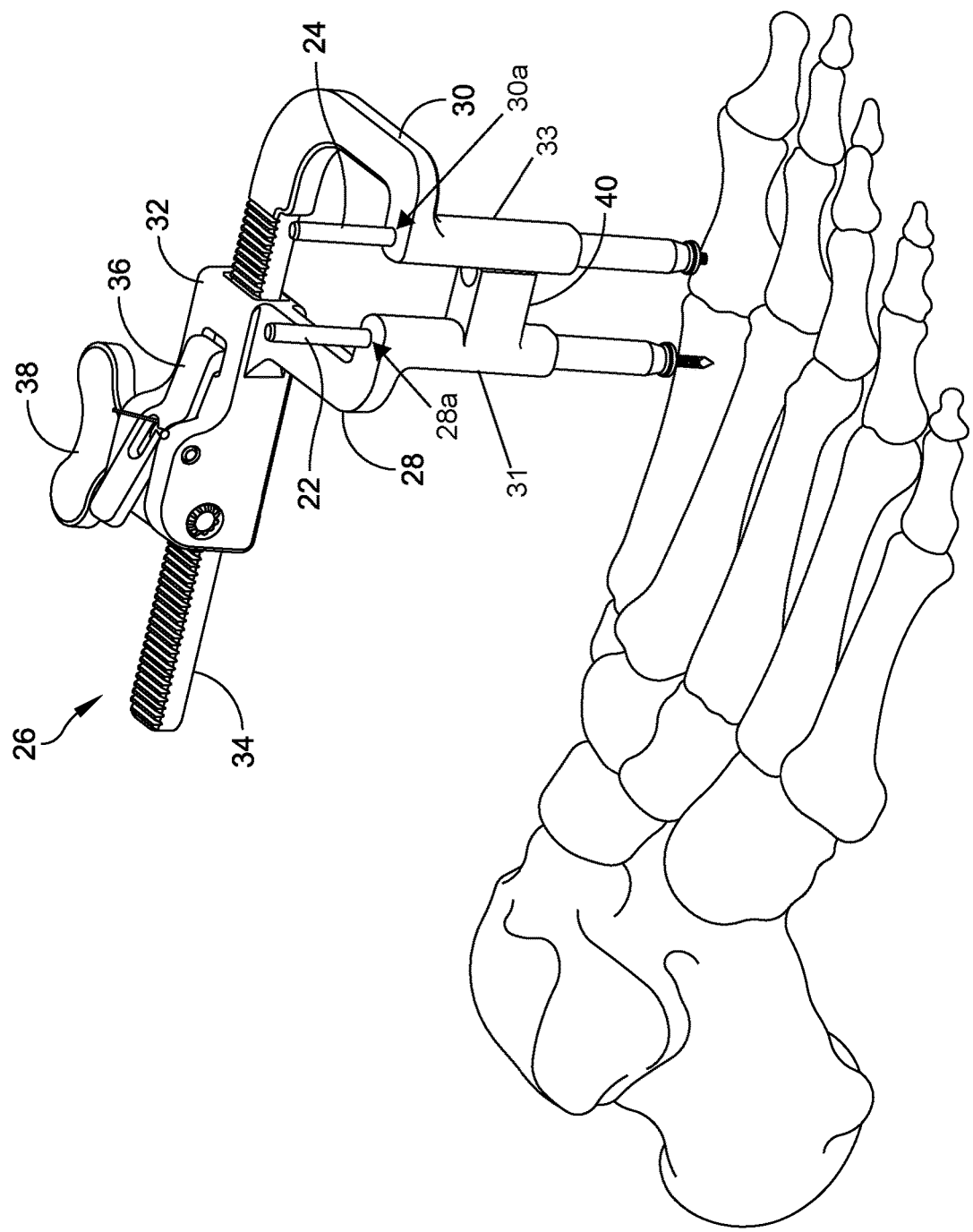
FIG. 5 shows a step of a method of performing a surgical procedure on an MTP joint in which a distractor is coupled to the pins.

As shown in FIG. 5, a distractor 26 is then engaged with the pins 22, 24. In some embodiments, the distractor 26 has a first arm 28 configured to engage the first pin 22 and a second arm 30 configured to engage the second pin 24. The first arm 28 and the second arm 30 are spaced apart along a longitudinal member 34. The first and second arms 28, 30 may define passages 28a, 30a, respectively, to receive a respective pin 22, 24. For example, the first arm 28 may include a cylindrical sleeve 31 extending downward (i.e., transverse to the longitudinal member 34) and defining passage 28a to receive the first pin 22 and the second arm 30 may include a cylindrical sleeve 33 extending downward (i.e., transverse to the longitudinal member 34) and defining the second passage 30a to receive the second pin 24. The first and second arms 28, 30 may also include means for fixing the arms 28, 30 to the respective pin 22, 24 (e.g., a collet, threads, etc.). The first arm 28 and the second arm 30 are translatable with respect to one another such that the distractor 26 can be used to increase and/or decrease the distance between the pins 22, 24 and, thereby, increase and/or decrease the distance between the metatarsal 200 and proximal phalanx 202.

For example, as shown in FIG. 5, the first arm may extend from a mounting block 32 that is translatable along the longitudinal member 34. The second arm 30 extends from a first end of the longitudinal member 34 and may be fixed in position relative to the longitudinal member 34. For example, the second arm 30 may be integrally formed with the longitudinal member 34. In some embodiments, the longitudinal member 34 includes ratchet teeth and the mounting block 32 is coupled to a pawl 36. The pawl 36 is configured to engage the ratchet teeth to control movement of the mounting block 32 along the longitudinal member. The mounting block 32 may also be coupled to an adjustment knob 38 that allows the user to control movement of the mounting block 32 along the longitudinal member 34 to adjust the distance between the first arm 28 and the second arm 30 and, thereby, the distance between the first pin 22 and the second pin 24. Similar distractors that can be adapted to be used with the geared instrument 2 are described in U.S. Pat. No. 9,770,272, issued Sep. 26, 2017, entitled ORTHOPEDIC COMPRESSION/DISTRACTION DEVICE, and PCT patent application publication no. WO 2015/137976, published Sep. 17, 2015, entitled ORTHOPEDIC COMPRESSION/DISTRACTION DEVICE, both of which are incorporated herein by reference in their entireties.

Although the movable arm (first arm 28) is shown in engagement with the pin that is inserted in the metatarsal 200, it should be understood that other orientations of the distractor 26 can be used. For example, the movable arm (first arm 28) may be engaged with the pin that is inserted in the proximal phalanx 202. Further, in some embodiments, both arms 28, 30 may be translatable along the longitudinal member 34.

Figure 6:
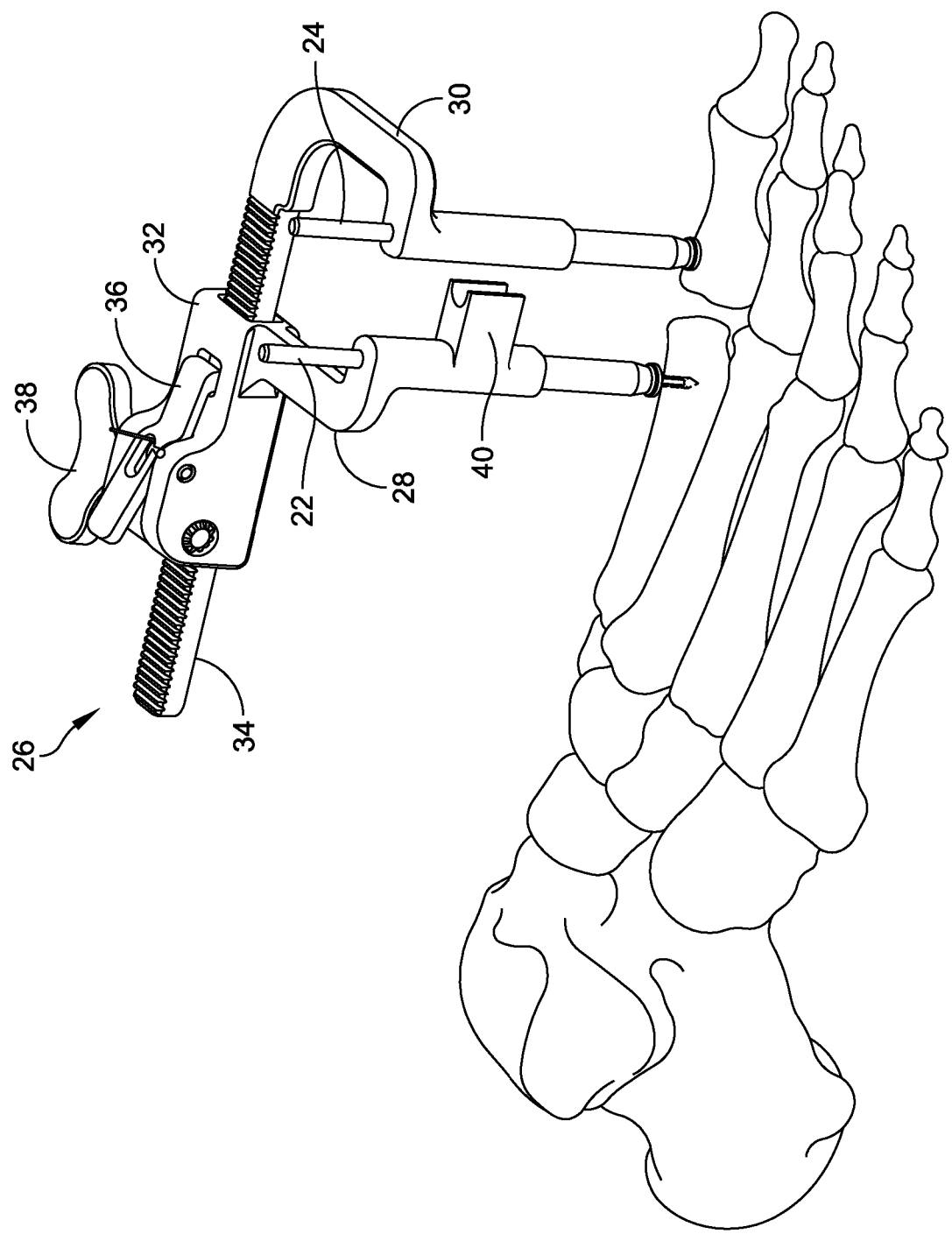
FIG. 6 shows a step of a method of performing a surgical procedure on an MTP joint in which the metatarsal and proximal phalanx are separated.

As shown in FIG. 6, the distance between the metatarsal 200 and the proximal phalanx 202 can be increased using the distractor 26. For example, a surgeon can increase this distance by translating the mounting block 32 along the longitudinal member 34 (e.g., by rotating the knob 38). With the first arm 28 in the desired position, the pawl 36 engages one or more ratchet teeth on the longitudinal member 34 to restrict movement of the first arm 28 along the longitudinal member 34. Optionally, the distractor 26 may include a means for locking the arms 28, 30 in the desired position to prevent inadvertent movement of the arms 28, 30 (e.g., a set screw).

FIG. 7 shows the geared instrument 2 inserted into the space between the metatarsal 200 and the proximal phalanx 202. As shown, in some embodiments, the distractor 26 includes a retainer 40 for holding the geared instrument 2 in position. For example, the retainer 40 may extend from first arm 28 (e.g., parallel to the longitudinal member 34) and define a cavity within which housing 10 of geared instrument 2 is retained. In some embodiments, retainer 40 may include fingers defining the cavity and configured to engage the housing 10 to hold it in position. For example, the fingers may flex during insertion of the housing 10 such that the fingers grasp the housing 10 to retain the geared instrument 2. In some embodiments, when the geared instrument 2 is coupled to the retainer 40, the distance from the center of the first pin 22 to the longitudinal axis 6 is between about 10 mm and about 20 mm. In other embodiments (not shown), the retainer 40 extends from the second arm 30. In such embodiments, the distance from the center of the second pin 24 to the longitudinal axis 6 may be between about 10 mm and about 20 mm.

Once the geared instrument 2 is positioned in the MTP joint, the reamer 18 may be used to perform a surgical procedure (e.g., remove cartilage from the joint). As the shaft 4 is rotated, the reamer 18 rotates and removes material (e.g., cartilage or bone) from the joint space. As the reamer rotates, the arms 28, 30 may be moved closer to one another to decrease the space between the metatarsal 200 and the proximal phalanx 202, thereby allowing the reamer 18 to continue to remove material. Optionally, after preparing one side of the MTP joint, the geared instrument 2 may be removed from the joint and rotated to prepare the other of the metatarsal 200 and phalanx 202, as described above.

Alternatively, as described above, in some embodiments, the geared instrument 2 includes two reamers 18a, 18b extending in opposite directions such that both bones can be prepared simultaneously. FIG. 11 shows such an embodiment in use. As can be seen in FIG. 11, the geared instrument may be positioned such that the cone reamer 18b is oriented toward the first metatarsal 200 and the cup reamer 18a is oriented toward the proximal phalanx 202. In such embodiments, rotation of the shaft 4 is translated to rotation of both the cup reamer 18a and the cone reamer 18b. As a result, material may be removed from both bones simultaneously. This may reduce the total amount of time needed to perform the procedure.

In some embodiments, an irrigation clip is attached to the distractor 26 or otherwise directed at the MTP joint to flush the joint space during or after operation of geared instrument 2. Suction may also be used to remove tissue and excess fluids from the joint space.

Figure 8:
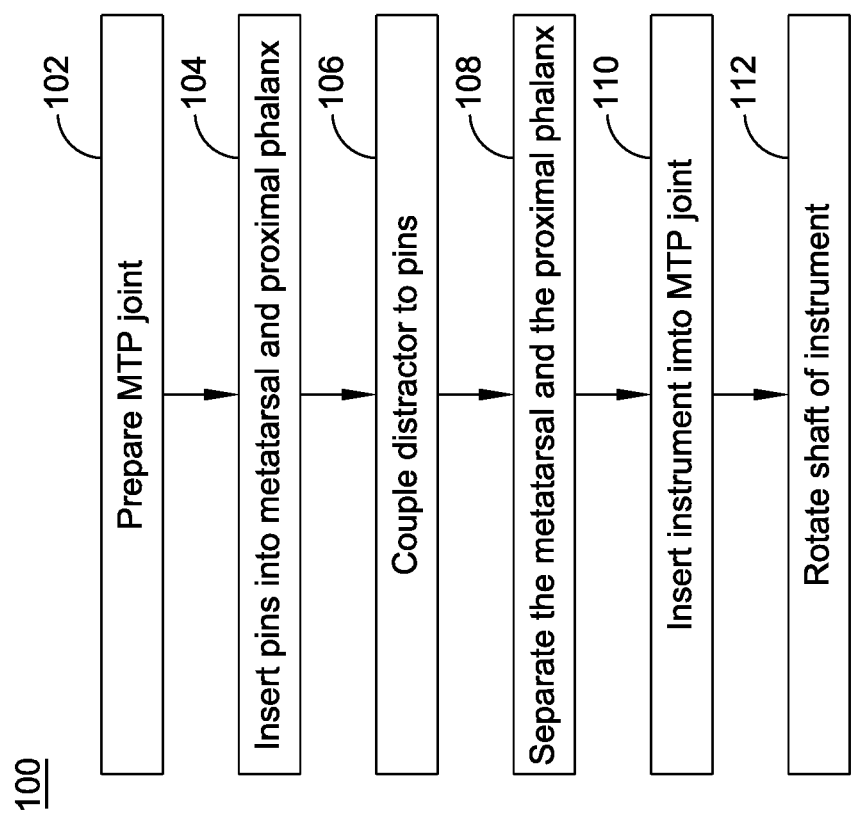
FIG. 8 is a flowchart illustrating a method of performing a surgical procedure on an MTP joint.

FIG. 8 is a flowchart further illustrating one embodiment of a method 100 of performing a surgical procedure using the geared instrument 2 and distractor 26. In step 102, an MTP joint is prepared to receive the geared instrument 2. Preparation of the MTP joint may include, for example, forming an incision (e.g., a superior incision). In step 104, pins 22, 24 are inserted into the metatarsal 200 and proximal phalanx 202, respectively. In some embodiments, the positioning of the pins 22, 24 may be guided using fluoroscopy or other imaging modalities to ensure that the distance between the pins 22, 24 and the end of the respective bone is appropriate. In step 106, the distractor 26 is coupled to the pins. In step 108, the distractor is used to separate the metatarsal 200 and the proximal phalanx 202. In step 110, the geared instrument 2 is inserted into the MTP joint. In step 112, the shaft 4 of the geared instrument 2 is rotated, thereby rotating reamer 18 to remove cartilage and/or bone from the MTP joint and otherwise prepare the joint for fusion. While the shaft 4 is rotated, the arms 28, 30 of the distractor 26 may be moved toward one another such that the metatarsal 200 and proximal phalanx 202 move closer to allow the reamer 18 to remove additional material.

Alternatively, or additionally, in some embodiments, one of first pin 22 and second pin 24 is inserted into its respective bone. The distractor 26 is then engaged with the pin that is inserted into the bone. The distractor 26 is then used as a guide for insertion of the other of the first pin 22 and the second pin 24. After placement of the pins 22, 24, the procedure may be performed as described above.

In various embodiments, a geared instrument (e.g., instrument 2) and a distractor (e.g., distractor 26) may be provided together as a kit or system. This may simplify preparation for, and performance of, procedures, such as those described above. In addition, instruments and distractors of various sizes and configurations (e.g., left and right) may be provided together to accommodate the patient's anatomy or the user's preference.

While the foregoing description and drawings represent preferred or exemplary embodiments of the present invention, it will be understood that various additions, modifications and substitutions may be made therein without departing from the spirit and scope and range of equivalents of the accompanying claims. In particular, it will be clear to those skilled in the art that the present invention may be embodied in other forms, structures, arrangements, proportions, sizes, and with other elements, materials, and components, without departing from the spirit or essential characteristics thereof. One skilled in the art will further appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims and equivalents thereof, and not limited to the foregoing description or embodiments. Rather, the appended claims should be construed broadly, to include other variants and embodiments of the invention, which may be made by those skilled in the art without departing from the scope and range of equivalents of the invention. All patents and published patent applications identified herein are incorporated herein by reference in their entireties.

What is claimed is:

1. A system, comprising:
   an instrument, comprising:
   a shaft extending from a first end to a second end and defining a first axis between the first end and the second end;
   a first gear coupled to the first end of the shaft such that rotation of the shaft about the first axis causes rotation of the first gear about the first axis;
   a second gear enmeshed with the first gear;
   a reamer coupled to the second gear; and
   a third gear enmeshed with the first gear and a second reamer coupled to the third gear;
   wherein rotation of the shaft about the first axis causes rotation of the reamer about a second axis that is non-parallel with the first axis such that, with the instrument at least partially disposed in a joint space between a first bone and a second bone, rotation of the reamer removes material from the joint space such that the second reamer extends in a different direction than the reamer such that, when the instrument is at least partially disposed in the joint space, the reamer faces the first bone and the second reamer faces the second bone; and
   a distractor, comprising:
   a first arm defining a first passage configured to receive a first pin inserted in the first bone;
   a second arm defining a second passage configured to receive a second pin inserted in the second bone; and
   a retainer extending from the first arm, wherein the retainer is configured to engage the instrument to retain the instrument in position;
   wherein the distance between the first passage and the second passage is adjustable.

2. The system of claim 1, wherein the instrument further comprises a housing, and the shaft is at least partially disposed in the housing.

3. The system of claim 1, wherein the second end of the shaft is configured to be engaged by a mechanical driver.

4. The system of claim 1, wherein the distractor further comprises an elongated member, and wherein the distance between the first passage and the second passage is adjustable by translating the first arm along the elongated member.

5. The system of claim 1, wherein each of the first gear and the second gear are spiral bevel gears.

6. The system of claim 1, wherein the reamer is a cup reamer.

7. The system of claim 1, wherein the reamer is a cone reamer.

8. The system of claim 1, wherein the instrument is configured to be at least partially inserted in a metatarsophalangeal joint.

9. The system of claim 1, wherein the reamer is a cup reamer and the second reamer is a cone reamer.

10. A method, comprising:
    forming an incision to access a metatarsophalangeal joint;
    locating an instrument partially within the metatarsophalangeal joint, the instrument comprising:
    a shaft extending from a first end to a second end and defining a first axis between the first end and the second end;
    a first gear coupled to the first end of the shaft such that rotation of the shaft about the first axis causes rotation of the first gear about the first axis;
    a second gear enmeshed with the first gear;
    a reamer coupled to the second gear and;
    a third gear enmeshed with the first gear and a second reamer coupled to the third gear;
    wherein rotation of the shaft about the first axis causes rotation of the reamer about a second axis that is non-parallel with the first axis; and
    rotating the shaft about the first axis to rotate the reamer about the second axis to remove material from the metatarsophalangeal joint wherein the second reamer extends in a different direction than the reamer such that, when the instrument is at least partially disposed in the joint space, the reamer faces the first bone and the second reamer faces the second bone;
    inserting a first pin into a first passage formed in a first arm configured to direct a first pin into engagement with a first bone of the metatarsophalangeal joint;
    inserting a second pin into a second passage formed in a second arm configured to direct a second pin into engagement with a second bone of the metatarsophalangeal joint;
    holding the instrument in position with a retainer extending from the first arm; and
    adjusting the distance between the first passage and the second passage.

11. The method of claim 10, further comprising inserting a first pin into a metatarsal and inserting a second pin into a proximal phalanx of the metatarsophalangeal joint.

12. The method of claim 11, further comprising coupling a first arm of a distractor to the first pin and a second arm of the distractor to the second pin.

13. The method of claim 12, further comprising adjusting the distance between the first pin and the second pin such that a distance between the metatarsal and the proximal phalanx is increased.

14. An instrument, comprising:
    a shaft extending from a first end to a second end and defining a first axis between the first end and the second end;
    a first gear coupled to the first end of the shaft such that rotation of the shaft about the first axis causes rotation of the first gear about the first axis;
    a second gear enmeshed with the first gear;
    a reamer coupled to the second gear; and
    a third gear enmeshed with the first gear and a second reamer coupled to the third gear;
    wherein rotation of the shaft about the first axis causes rotation of the reamer about a second axis that is non-parallel with the first axis such that, with the instrument at least partially disposed in a joint space between a first bone and a second bone, rotation of the reamer removes material from the joint space such that the second reamer extends in a different direction than the reamer such that, when the instrument is at least partially disposed in the joint space, the reamer faces the first bone and the second reamer faces the second bone; and
    wherein the reamer is one of a cup reamer and a cone reamer.

15. The instrument of claim 14, further comprising a housing, and wherein the shaft is at least partially disposed in the housing.

16. The instrument of claim 14, wherein the second end of the shaft is configured to be engaged by a mechanical driver.

17. The instrument of claim 14, wherein the reamer is a cup reamer.

18. The instrument of claim 14, wherein the reamer is a cone reamer.

19. The instrument of claim 14, wherein the instrument is configured to be at least partially inserted in a metatarsophalangeal joint.

20. The instrument of claim 14, wherein the reamer is a cup reamer and the second reamer is a cone reamer.

* * * * *